(12) United States Patent
Chen

(10) Patent No.: US 9,358,081 B2
(45) Date of Patent: Jun. 7, 2016

(54) LINGUAL BRACKET

(76) Inventor: Qifeng Chen, Fujian (CN)

(*) Notice: Subject to any disclaimer, the term of this patent is extended or adjusted under 35 U.S.C. 154(b) by 113 days.

(21) Appl. No.: 13/818,266

(22) PCT Filed: Aug. 1, 2011

(86) PCT No.: PCT/CN2011/077851
§ 371 (c)(1),
(2), (4) Date: Feb. 21, 2013

(87) PCT Pub. No.: WO2012/025004
PCT Pub. Date: Mar. 1, 2012

(65) Prior Publication Data
US 2013/0157214 A1  Jun. 20, 2013

(30) Foreign Application Priority Data
Aug. 25, 2010 (CN) .......................... 2010 1 0262798

(51) Int. Cl.
*A61C 3/00* (2006.01)
*A61C 7/30* (2006.01)
*A61C 7/14* (2006.01)

(52) U.S. Cl.
CPC .................. *A61C 7/303* (2013.01); *A61C 7/145* (2013.01)

(58) Field of Classification Search
CPC ............ A61C 7/12; A61C 7/14; A61C 7/141; A61C 7/145; A61C 7/148; A61C 7/16; A61C 7/285; A61C 7/287; A61C 7/30; A61C 7/303
USPC .......................... 433/8–11, 13, 14, 16, 18, 21
See application file for complete search history.

(56) References Cited

U.S. PATENT DOCUMENTS

| 6,139,317 | A  | * | 10/2000 | Goldschmied ................. 433/14 |
| 7,419,375 | B2 |   | 9/2008  | Farzin-Nia et al. |
| 7,500,851 | B2 |   | 3/2009  | Williams |
| 7,621,743 | B2 |   | 11/2009 | Bathen et al. |
| 2008/0003535 | A1 | | 1/2008 | Williams |

FOREIGN PATENT DOCUMENTS

| CN | 201005796 Y | 1/2008 |
| CN | 101692984 A | 4/2010 |
| CN | 201492528 U | 6/2010 |
| CN | 101912312 A | 12/2010 |
| CN | 201861779 U | 6/2011 |
| JP | 2005058742 A | 3/2005 |
| JP | 2006320726 A | 11/2006 |

OTHER PUBLICATIONS

Machine translation of CN 101692984, Qifeng Chen, Apr. 14, 2010.*

* cited by examiner

*Primary Examiner* — Matthew Nelson
(74) *Attorney, Agent, or Firm* — Blank Rome LLP

(57) ABSTRACT

A lingual bracket has a bracket body (1) and a movable wing (2). The bracket body (1) includes a bracket seat (11) with non-skid pattern on its lower surface and a stationary wing (12) integrally and protrudingly provided onto an end of the bracket seat. A through hole (13) is arranged along the central axis of the stationary wing (12). A movable wing (2) has an arch wire hook (21) at an end and a fixed portion (22) at the other end. The fixed portion end of the movable wing passes through the through hole in the stationary wing, and a spring (3) is sleeved on the section of the movable wing passing through the through hole. One end of the spring (3) is engaged against the stationary wing (12), and the other end is retained on the fixed portion of the movable wing. The arch wire hook (21) of the movable wing (2) can hook an arch wire (4) by constant orthodontic force provided by the spring (3).

12 Claims, 5 Drawing Sheets

LINGUAL BRACKET

RELATED APPLICATIONS

This application is a National Phase of Application No. PCT/CN2011/077851 filed Aug. 1, 2011, which claims the benefit of Chinese Patent Application No. 201010262798.9 filed on Aug. 25, 2010, which are incorporated herein by reference in their entirety

FIELD OF THE INVENTION

The present invention pertains to the field of medical appliance and more particularly, to an orthodontic lingual bracket.

DESCRIPTION OF THE PRIOR ART

An orthodontic bracket in prior art has a body having two lateral wings protrudingly arranged on the upper surface thereof and a bracket seat with non-skid pattern on the lower surface thereof, and a groove for receiving an arch wire formed between the two lateral wings. The two lateral wings are symmetrically disposed at two sides of the body, and the central plane of the wings coincides with the central plane of the bracket seat, thus forming a stable unit. Invisible lingual orthodontic technology emerges in 1970's and is very popular with a great many patients, especially adults, for the reason that the bracket of the appliance sticks to the lingual side of the teeth hides well and would not affect the appearance and social activity. However, since the great individual differences occurred in the lingual side of the teeth, especially in tooth thickness (tooth protruding distance) and torque angle, traditional lingual bracket adopts fixed groove. The bottom thickness of the bracket and the predetermined torque angle are unchangeable, so the bracket can hardly match the individual tooth. Doctors have to bend arch wires substantially to compensate the differences clinically. But it is very difficult to achieve individualized matching by bending arch wires due to limited lingual vision and intraoral space and the like, which impedes doctors to use and spread clinically, and additionally, the medical cost is much higher than tooth surface orthodontic therapy. It becomes an object of the present invention to develop a bracket suitable for the orthodontic lingual therapy.

SUMMARY OF THE INVENTION

The main object of the present invention is to provide a lingual bracket having a spring pivoted between the movable wing and the bracket body to apply a constant orthodontic force provided by the spring force of the spring.

The scheme of the present invention is achieved as following: a lingual bracket, including a bracket body and a movable wing, characterized in that, the bracket body comprises a bracket seat with non-skid pattern on its lower surface and a stationary wing integrally and protrudingly provided onto an end of the bracket seat, a through hole is arranged along the central axis of the stationary wing; a movable wing has an arch wire hook at an end and a fixed portion at the other end; the fixed portion end of the movable wing passes through the through hole in the stationary wing and a spring sleeves on the section of the movable wing passing through the through hole, with one end engaged against the stationary wing, and the other end retained on the fixed portion of the movable wing. The arch wire hook of the movable wing can hook an arch wire to correct the tooth in accordance with the predetermined style of the arch wire by constant orthodontic force provided by the spring.

The movable wing has an arch wire hook integrally with a tie hook extending to an opposite direction from the back of the arch wire hook, and the stationary wing is integrated with a tie wing at the side facing the bracket seat. The tie wing cooperates with the tie hook at the side of the movable wing to form a complete wing for the elastic tie ring to tie.

The fixed portion of the movable wing can be of one of the following several structures:

The fixed portion of the movable wing is a machined T-shape head, and one end of the spring can be engaged against the T-shape head.

The fixed portion of the movable wing is a deformed bending section which can press one end of the spring.

The fixed portion of the movable wing is a bifurcate structure which can deform and bend outwardly in opposite direction, so that one end of spring can be engaged and retained at the bending part of the bifurcation.

The fixed portion of the movable wing is a through hole, and one end of the spring can pass through the through hole to be retained.

The distal end of the bracket seat away from the stationary wing is arranged with an auxiliary tubular hole that can directly allow high elastic arch wire to pass therethrough, and as the auxiliary tubular hole is positioned closely to the tooth surface, the tooth alignment can be facilitated.

Both of the bracket seat of the bracket body and the movable wing are an arch structure matching the lingual tooth surface, which not only can fixedly match with tooth surface, but also can provide larger orthodontic force.

The arch wire hook of the movable wing is orderly arranged with a groove and a tie hook on the back of the arch wire hook. The groove cooperates with the arch wire to create horizontal orthodontic force.

The present invention has a spring pivoted between the movable wing and the bracket body and applying constant spring force to teeth, which can bring greater deformation stroke, long lasting and smoother orthodontic force so as to avoid the falloff tendency and the uncontrollable quantity of the force provided by the elastic tie ring to realize the orthodontics of the larger malposition, and to avoid replacing arch wire frequently nor making tie ring again to improve the efficiency. Besides, the presence of the spring can overcome the drawback of losing predetermined elastic force of traditional tie ring resulted from the pulling deformation while tied or swelling by soaked in saliva. Further, the movable wing and the bracket body are respectively arranged with tie wing and tie hook which can cooperate with each other and provide places for elastic tie ring to tie on. The spring and the elastic tie spring can be used alone or in combination to apply orthodontic force, alternatively, in a way depending on the or to the orthodontic therapy, in order to further enhance orthodontic efficiency. Still further, the auxiliary tubular hole arranged in the bracket body is closer to the tooth surface, and with the high elastic arch wire, so it is easier to align teeth and thus achieve profitable effect.

BRIEF DESCRIPTION OF THE DRAWINGS

Hereinafter further description will be made by incorporating figures to illustrate the present invention.

Wherein:

| 1—bracket body | 11—bracket seat | 12—stationary wing |
| --- | --- | --- |
| 13—through hole | 14—auxiliary tubular hole | 15—tie wing |
| 2—movable wing | 21—arch wire hook | 22—fixed portion |
| 23—tie hook | 24—groove | 3—spring |
| 4—arch wire | 5—tie ring | |

DETAILED DESCRIPTION OF THE PREFERRED EMBODIMENTS

Figure 1:
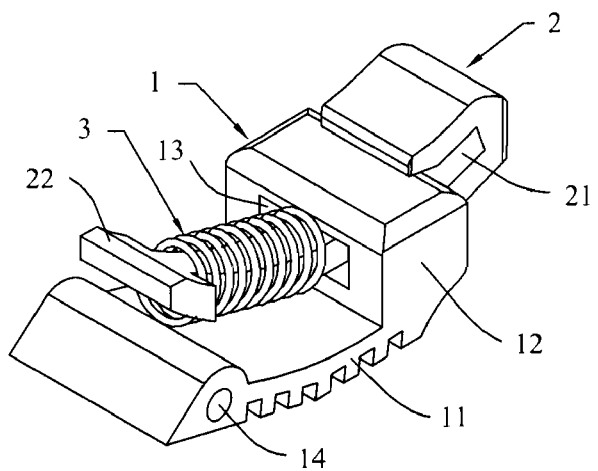
FIG. 1 is a perspective schematic view of a lingual bracket.
Figure 2:
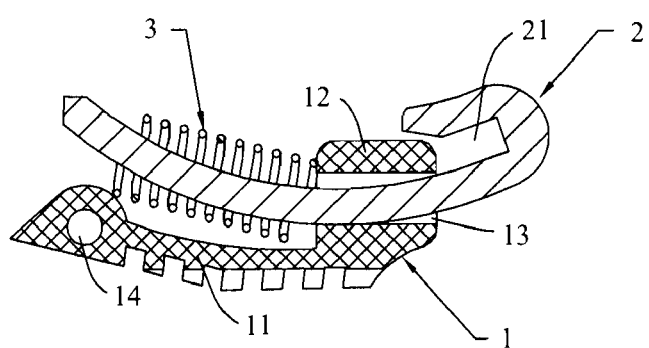
FIG. 2 is a cross-sectional schematic view of a lingual bracket.

Refer to FIGS. 1 and 2, the lingual bracket includes bracket body 1 comprising a bracket seat 11 with non-skid pattern on its lower surface and a stationary wing 12 integrally and protrudingly provided onto an end of bracket seat 11, and a movable wing 2. A through hole 13 is arranged along the central axis of stationary wing 12, in which movable wing 2 pivoted. A distal end of the bracket seat 11 away from the stationary wing 12 is arranged with an auxiliary tubular hole 14. The movable wing 2 has an arch wire hook 21 at an end and a fixed portion 22 at the other end used to limit or retain one end of spring 3. The fixed portion end of the movable wing 2 can pass through the through hole 13 in the stationary wing 12, and a spring 3 sleeves on the section of movable wing 2 that passes through the through hole 13; one end of the spring 3 is against the stationary wing 12, while the other end is retained on the fixed portion 22 of the movable wing 2. Clinically, secure the bracket body 1 to the lingual tooth surface by the bracket seat 11, and keep the stationary wing 12 facing downward; then let the fixed portion 22 of the movable wing 2 passing through the through hole 13 in the stationary wing 12 and thread the spring 3 into the section that passes through the movable wing 2 to be ready for use; then prepare the arch wire 4 by pulling down the arch wire hook 21 to hook the arch wire 4. By the spring force from spring, the bracket body tends to be pulled closely to one side of the arch wire 4, which provides a constant spring force to the teeth to be corrected.

It is known from the figures that, the auxiliary tubular hole 14 in bracket seat 11 is positioned closely to the tooth surface and can apply the orthodontic force caused by itself directly on the tooth surface when the high elastic arch wire passes through the auxiliary tubular hole 14, so as to align the tooth surface to be corrected, and to avoid the defect in traditional technology that it is not easy to precisely adjust the contact points of adjacent teeth caused by the long distance between the arch wire in the groove and the tooth surface, and the long arm of force of the arch wire. In addition, both of the bracket seat 11 of the bracket body 1 and the movable wing 2 are an arch structure matching the lingual tooth surface, which not only can secure onto the tooth surface, but also can provide larger orthodontic force.

Figure 3:
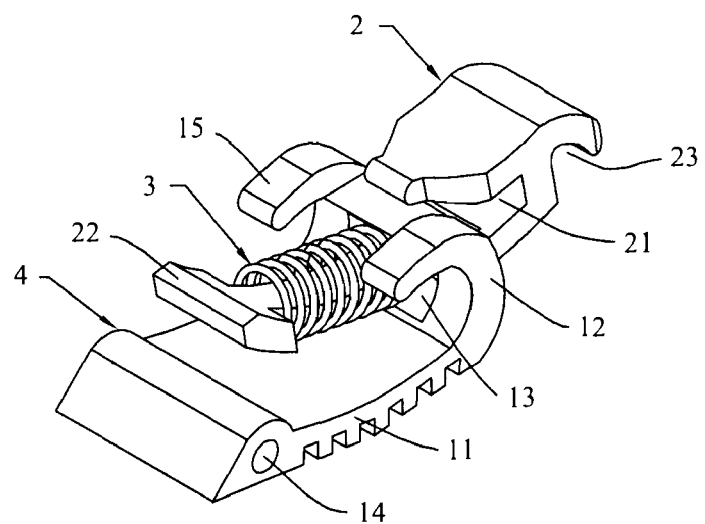
FIG. 3 is a perspective schematic view of a lingual bracket with a tie wing.
Figure 4:
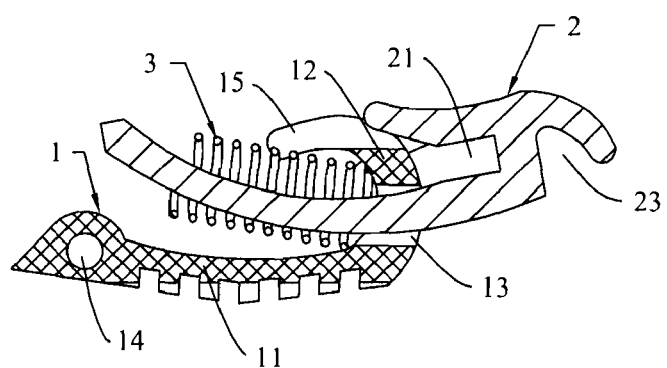
FIG. 4 is a cross-sectional schematic view of a lingual bracket with a tie wing.

Refer to FIGS. 3 and 4, the movable wing 2 has the arch wire hook 21 integrated with the tie hook 23 extending to an opposite direction from the back of the arch wire hook 21, and the stationary wing 12 is integrated with the tie wing 15 at the side facing the bracket seat 11, both of which cooperate with each other to form a complete tie wing to provide a special tie position for the tie ring.

Figure 5:
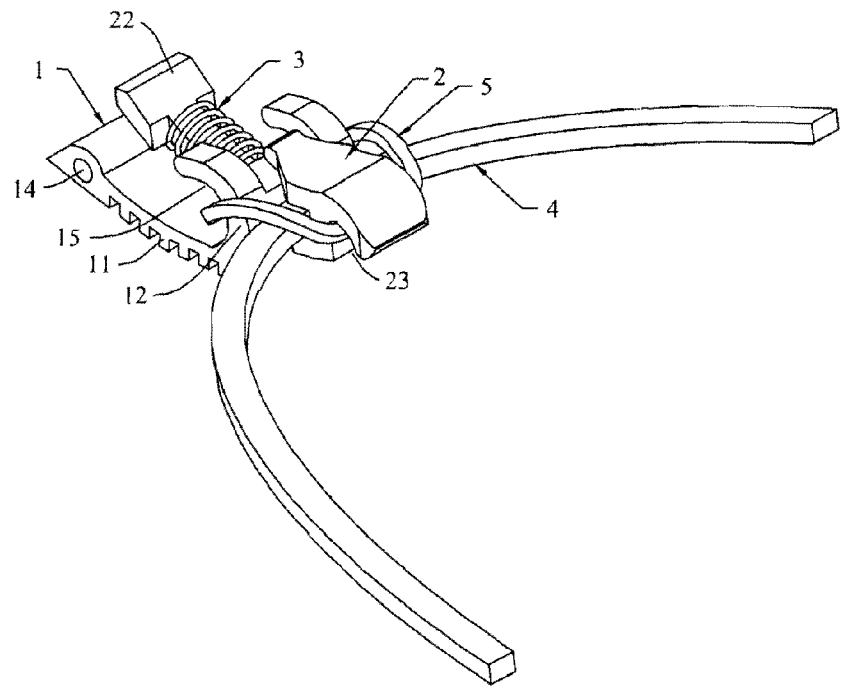
FIG. 5 is a schematic view of a lingual bracket in operation, with a tie wing.

Refer to FIG. 5, which is a view of a lingual bracket in operation, with a tie wing. A tie ring 5 can be tied between the tie wing 15 and the tie hook 23 to increase the orthodontic force, while the orthodontic force is the spring force of spring 3 plus the elastic force from the tie ring 5. Clinically, the spring 3 and the tie ring 5 can be used alone or in combination at later phase of correction. The three choices provide different orthodontic forces to meet various patients, thus to compensate for the traditional defect of the unchangeableness of the orthodontic bracket.

Figure 6:
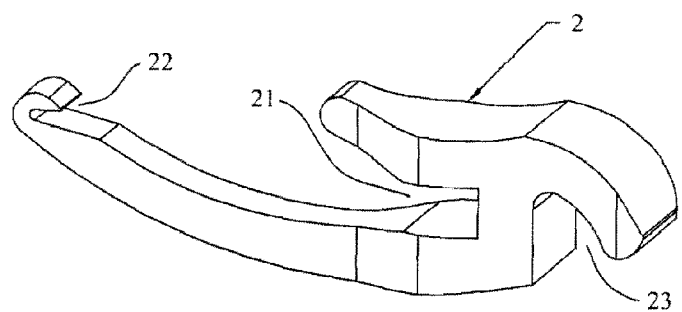
FIG. 6 is a perspective schematic view of a movable wing of a first embodiment.
Figure 7:
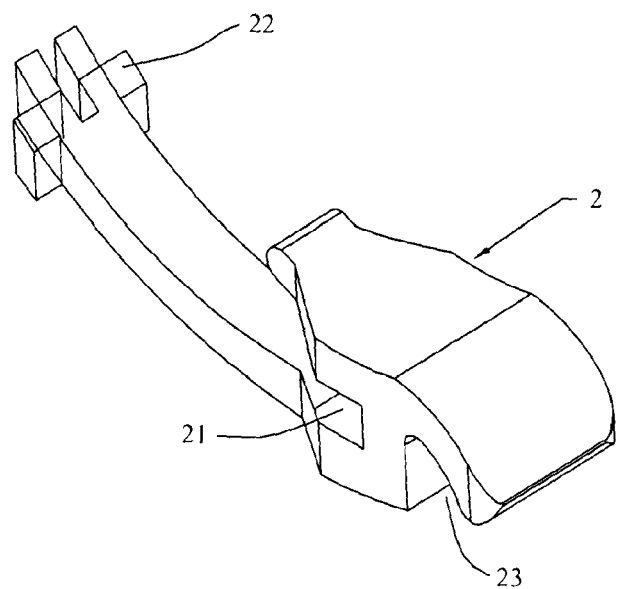
FIG. 7 is a perspective schematic view of a movable wing of a second embodiment.
Figure 8:
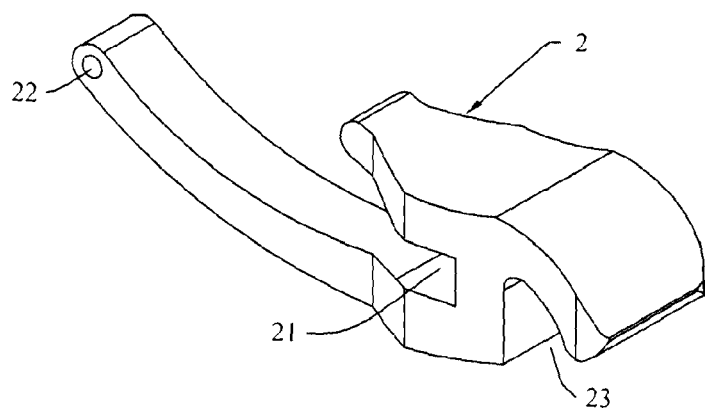
FIG. 8 is a perspective schematic view of a movable wing of a third embodiment.
Figure 9:
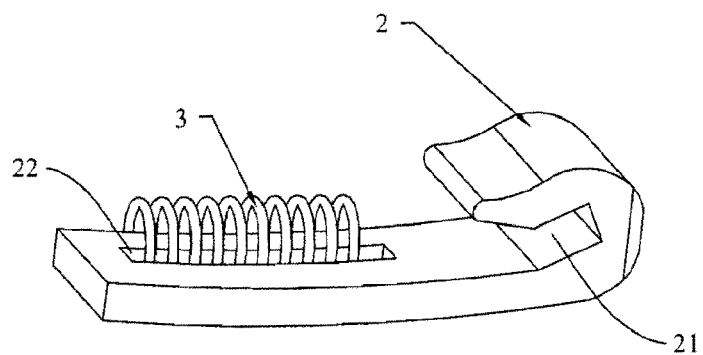
FIG. 9 is a perspective schematic view of a movable wing of a fourth embodiment.

Fixed portion 22 of movable wing 2 can be of various structures aiming to limit the spring 3 from sliding out and the force point of the spring force. The fixed portion 22 can be of T-shaped structure as seen in FIG. 5 to play the role of engaging and limiting; or as seen in FIG. 6, where the fixed portion 22 is a deformed bending section which presses one end of the spring 3 to play the role of engaging and limiting; or as seen in FIG. 7, where the fixed portion 22 is a bifurcate structure which can deform and bend outwardly in opposite direction, as shown by the dotted line in the figure, so that an end of the spring 3 can be against and retained to the bending deformation part of the bifurcation; or as seen in FIG. 8, where the fixed portion 22 is a through hole, through which an end of spring 3 can pass to be retained; or as seen in FIG. 9, where the fixed portion 22 is a groove hole, the spring 3 entirely rotates to sleeve on the side edge of the groove hole, and the fixed portion 22 of the said groove hole has two side edges, a wide one and a narrow one, the spring 3 can choose either side to sleeve on to be retained. In clinical operation, likewise, the fixed portion 22 of the movable wing can be passed through the through hole 13 in the stationary wing firstly, and then the spring 3 can be rotated and sleeved thereon, with one end engaged against the stationary wing 12, and the other end engaged against the end of the groove hole in the fixed portion 22.

Figure 10:
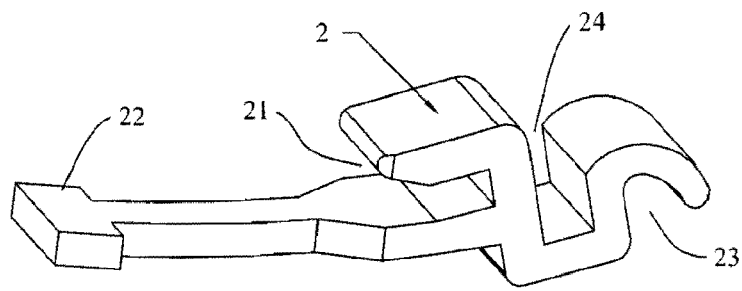
FIG. 10 is a perspective schematic view of a movable wing of a fifth embodiment.
Figure 11:
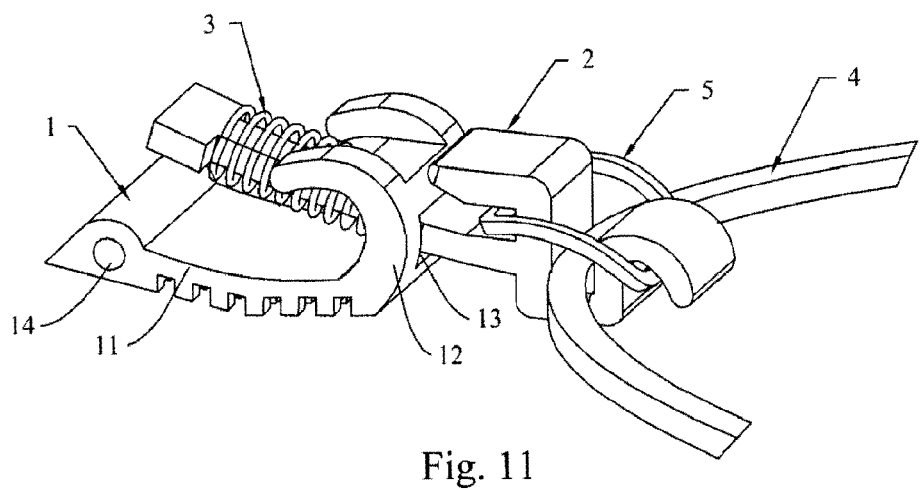
FIG. 11 is a schematic view of a lingual bracket in operation, with a groove.

Refer to FIGS. 10 and 11, the arch wire hook 21 of the movable wing is orderly arranged with a groove 24 and a tie hook 23 on the back of the arch wire hook. The arch wire 4 can be disposed in the groove 24, tied by the tie ring 5 and provide horizontal orthodontic force, while the spring 3 can also provide orthodontic force backward. If the arch wire 4 cooperates with the arch wire hook 21, vertical orthodontic force can then be obtained for clinical operation to utilize in combination depending on different situations.

The most obvious feature of the present invention is taking advantage of the spring force of spring, which can be applied on the teeth constantly to form an automatic constant tying without frequent replacement, and to overcome the difficulty of putting the arch wire into the groove in the initial phase by the arch wire being hooked by the arch wire hook of the movable wing and can not be detached throughout the orthodontic therapy. Therefore, the tie wing for tying can also be saved and be of smaller volume, especially in thickness, so that the sensation in the mouth of foreign body fades, and more hygienic. Another feature of the present invention is that the spring is threaded through the thread pitch clearance, which facilitates the replacement of springs with different elastic coefficient or movable wings of various structures.

The invention claimed is:

1. A lingual bracket, comprising:
a bracket body and a movable wing, wherein:
the bracket body comprises a bracket seat with a non-skid pattern on a lower surface thereof and a stationary wing integrally and protrudingly provided onto an end of the bracket seat, and the stationary wing has a through hole is arranged along a central axis of the stationary wing;
a movable wing has an arch wire hook at an end and a fixed portion at an opposing end of the movable wing and the fixed portion of the movable wing passes through the through hole in the stationary wing; and
a distal end of the bracket seat away from the stationary wing is arranged with an auxiliary tubular hole, and the auxiliary tubular hole is adapted to be positioned closely to a tooth surface;
a spring sleeves on a section of the movable wing passing through and extending out of the through hole, with one end of the spring engaged against an aspect of a frame of the through hole in the stationary wing facing the distal end of the bracket seat away from the stationary wing, and an opposing end of the spring retained on the fixed portion of the movable wing.

2. The lingual bracket according to claim 1, wherein the movable wing has an arch wire hook integrated with a tie hook extending to an opposite direction from back of the arch wire hook, and the stationary wing is integrated with a tie wing at a side facing the bracket seat.

3. The lingual bracket according to claim 1, wherein the fixed portion of the movable wing is a groove hole, the groove hole has a wide side edge and a narrow side edge, and the spring entirely rotates to and sleeves on the narrow edge.

4. The lingual bracket according to claim 3, wherein both of the bracket seat of the bracket body and the movable wing are arch structures matching the lingual tooth surface.

5. The lingual bracket according to claim 1, wherein the fixed portion of the movable wing is a machined T-shape head, and one end of the spring can be engaged against the T-shape head.

6. The lingual bracket according to claim 5, wherein both of the bracket seat of the bracket body and the movable wing are arch structures matching the lingual tooth surface.

7. The lingual bracket according to claim 6, wherein the arch wire hook of the movable wing is orderly arranged with a groove and a tie hook on back of the arch wire hook.

8. The lingual bracket according to claim 1, wherein the fixed portion of the movable wing is a deformed bending section which can press one end of the spring.

9. The lingual bracket according to claim 1, wherein the fixed portion of the movable wing is a bifurcate structure which can deform and bend outwardly in opposite directions, so that one end of the spring can be engaged and retained to the bending part of the bifurcate structure.

10. The lingual bracket according to claim 1, wherein the fixed portion of the movable wing is a through hole, and one end of the spring can pass through the through hole of the movable wing to be retained.

11. The lingual bracket according to claim 1, wherein the fixed portion of the movable wing is a groove hole, the groove hole has a wide side edge and a narrow side edge, and the spring entirely rotates to and sleeves on the wide edge.

12. The lingual bracket according to claim 11, wherein both of the bracket seat of the bracket body and the movable wing are arch structures matching the lingual tooth surface.

* * * * *